United States Patent
Kania et al.

(10) Patent No.: US 6,306,178 B1
(45) Date of Patent: Oct. 23, 2001

(54) PROSTHETIC DEVICE USING A CAM-SHAPED WHEEL

(75) Inventors: Bruce Kania, Bozeman; David Zimmerman, Pony, both of MT (US)

(73) Assignee: Fountainhead, Bozeman, MT (US)

( * ) Notice: Subject to any disclaimer, the term of this patent is extended or adjusted under 35 U.S.C. 154(b) by 0 days.

(21) Appl. No.: 09/422,466

(22) Filed: Oct. 21, 1999

Related U.S. Application Data

(60) Provisional application No. 60/105,532, filed on Oct. 22, 1998.

(51) Int. Cl.[7] ................... A61F 2/66; A61F 2/74
(52) U.S. Cl. ................... 623/52; 623/27
(58) Field of Search ................... 623/52, 51, 32, 623/28, 27, 40, 39

(56) References Cited

U.S. PATENT DOCUMENTS

| | | |
|---|---|---|
| 1,023,247 | 4/1912 | Frees . |
| 1,258,710 * | 3/1918 | Rowley ................... 623/39 |
| 3,453,663 * | 7/1969 | Minor ................... 623/27 |
| 3,820,169 * | 6/1974 | Long et al. ................... 623/39 |
| 4,169,453 | 10/1979 | Hunsicker . |
| 4,310,932 * | 1/1982 | Nader et al. ................... 623/39 |
| 4,457,288 | 7/1984 | Ricord . |
| 4,614,518 * | 9/1986 | Lehneis et al. ................... 623/39 |
| 4,669,445 | 6/1987 | Schaar . |
| 4,739,744 | 4/1988 | Nurney . |
| 4,756,296 | 7/1988 | Darlington . |
| 4,757,799 | 7/1988 | Bozek . |
| 4,770,154 | 9/1988 | Cook et al. . |
| 4,822,363 * | 4/1989 | Phillips ................... 623/27 |
| 4,887,582 | 12/1989 | Chattin . |
| 4,986,250 | 1/1991 | Darlington . |
| 5,040,520 | 8/1991 | Nurney . |
| 5,139,425 | 8/1992 | Daviet et al. . |
| 5,139,525 * | 8/1992 | Kristinsson ................... 623/55 |
| 5,314,499 | 5/1994 | Collier, Jr. . |
| 5,368,006 | 11/1994 | McPherson . |
| 5,376,139 | 12/1994 | Pitkin . |
| 5,376,141 | 12/1994 | Phillips . |
| 5,388,564 | 2/1995 | Islas . |
| 5,405,408 * | 4/1995 | Pitkin ................... 623/44 |
| 5,443,528 | 8/1995 | Allen . |
| 5,505,185 | 4/1996 | Miller . |
| 5,571,213 | 11/1996 | Allen . |
| 5,649,522 | 7/1997 | Troncoso . |
| 5,653,767 | 8/1997 | Allen et al. . |
| 5,653,768 | 8/1997 | Kania . |
| 5,695,527 | 12/1997 | Allen . |
| 5,782,229 | 7/1998 | Evans et al. . |
| 5,800,568 | 9/1998 | Atkinson et al. . |
| 5,809,982 | 9/1998 | McPherson . |
| 5,941,913 | 8/1999 | Wollnough et al. . |

* cited by examiner

Primary Examiner—David H. Willse
Assistant Examiner—Alvin Stewart
(74) Attorney, Agent, or Firm—Oblon, Spivak, McClelland, Maier & Neustadt, P.C.

(57) ABSTRACT

A prosthetic device includes an energy storing member, a lever member attached to the energy storing member, a rocking member and an energy transfer line. This line has a first end attached to a front end of the energy storing member and a second end attached to a back end of the lever member. The line has its middle portion attached to the rocking member. The energy storing member is preferably a leaf spring. This combination of elements in the prosthetic device may be a lower leg or foot for use by a below-the-knee amputee to simulate more closely the natural gait of a person while walking or running.

27 Claims, 4 Drawing Sheets

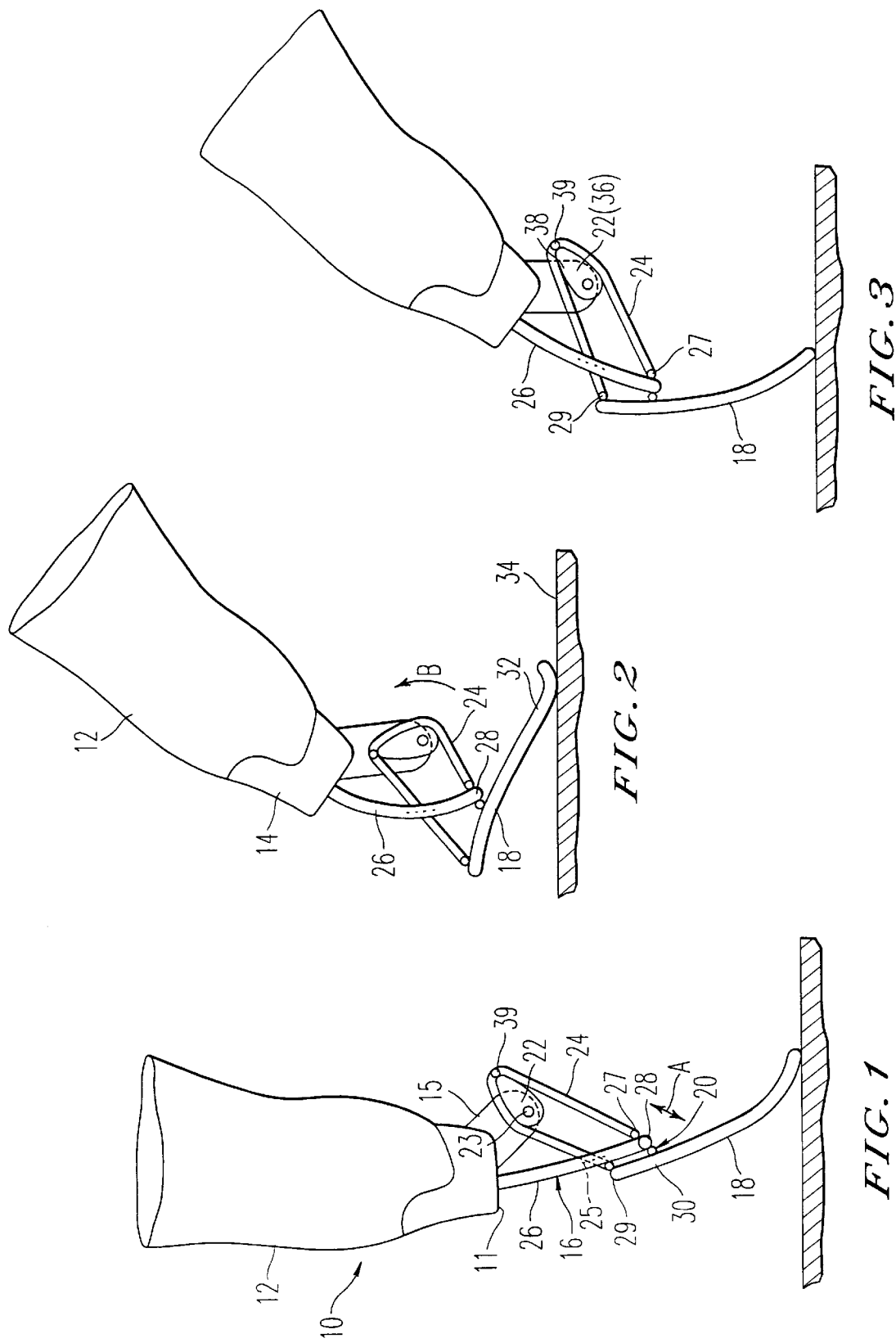

US 6,306,178 B1

PROSTHETIC DEVICE USING A CAM-SHAPED WHEEL

CROSS-REFERENCE TO RELATED APPLICATION

This application is related to U.S. Provisional Patent Application Ser. No. 60/105,532, filed Oct. 22, 1998, from which priority is claimed.

BACKGROUND OF THE INVENTION

1. Field of the Invention

The present invention relates to a prosthetic device for a lower leg or foot for use by a below-the-knee amputee.

2. Description of the Related Art

Although prosthetic devices have been in use for centuries, not until relatively recently have efforts been made to design prosthetic legs and feet to react dynamically to the cyclic loading and unloading of the foot during movement to simulate more closely natural gait. To this end, prosthetic devices typically are configured to store and release energy during normal body movements. Typical prosthetic feet include a spring plate arranged longitudinally approximately within the sole of a shoe. The spring plate is usually arranged so as to provide flexure of the foot while walking.

Materials undergo a certain amount of deformation when they are stressed. If a mechanical element experiences a steady deformation when acted upon by steady forces, it is exhibiting compliance which is the basic characteristic of a spring. A translational spring is a mechanical element which deforms by steady amounts when loaded by steady forces. A linear spring has a proportional relation between deformation and force. Thus, the spring stores work as energy associated with its deformation. This stored energy is called translational potential energy. Hence, the energy stored in the spring depends directly on the force transmitted to the spring. In other words, the work done by any force acting on a spring during a specified displacement is equal to the change in the kinetic energy of the spring. This statement is the basic work-energy principle of body dynamics in physics.

The single spring plate of the prior art may have varying thicknesses along its length to give varying compliances across the spring plate in order to simulate more closely the curling movement of a foot during a walking motion. Improvements to the spring plate have included multiple plates of different thicknesses attached or adhered to each other within the prosthetic foot in order to create different compliances along the length of the foot. However, these attempts to achieve different compliances by varying the thicknesses have not been successful because it has been found that spring plates are inherently limited in their simulation of the natural motion of a foot. In particular, as a prosthetic foot using such a spring plate is curled, as it is during a normal walking or running motion, the effort required to curl the prosthetic foot increases, thereby inhibiting the full range of motion. Therefore, it is desirable to provide a prosthetic device that provides a more natural simulation of the motion of a leg or a foot.

SUMMARY OF THE INVENTION

Accordingly, it is an object of the present invention to provide a prosthetic device which more naturally simulates the motion of a user's leg or foot.

According to the invention, the prosthetic device is provided with a base portion, a leaf spring attached to the base portion, a lever member hingedly attached to the leaf spring, a rocking member attached to the base portion, and a line having a first end attached to a front end of the leaf spring and having a second end attached to a back end of the lever member. The line has a middle portion, between the first and second ends, that is attached to the rocking member. The prosthetic device can convert a pivoting motion of the lever member into a deflection of the leaf spring, thereby storing energy imparted by the lever member to the leaf spring.

Preferably, the rocking member is an eccentric body, such as a cam-shaped wheel. The line is fixed to the eccentric body such that, as the lever member pivots, the amount of deflection caused in the leaf spring by the pulling of the line changes through the range of foot motion. Accordingly, the eccentric body can be configured such that the deflection of the leaf spring changes over the range of pivoting of the lever member.

BRIEF DESCRIPTION OF THE DRAWINGS

A more complete appreciation of the invention and many of the attendant advantageous thereof will be readily obtained as the same becomes better understood by reference to the following detailed description when considered in connection with the accompanying drawings, wherein:

FIG. 1 is a side elevational view of a first embodiment of the present invention at the beginning of a step;

FIG. 2 is a side elevational view of the embodiment shown in FIG. 1 at the midpoint of a step;

FIG. 3 is a side elevational view of the embodiment shown in FIG. 1 at the completion of a step;

DETAILED DESCRIPTION OF THE PREFERRED EMBODIMENTS

Figure 5:
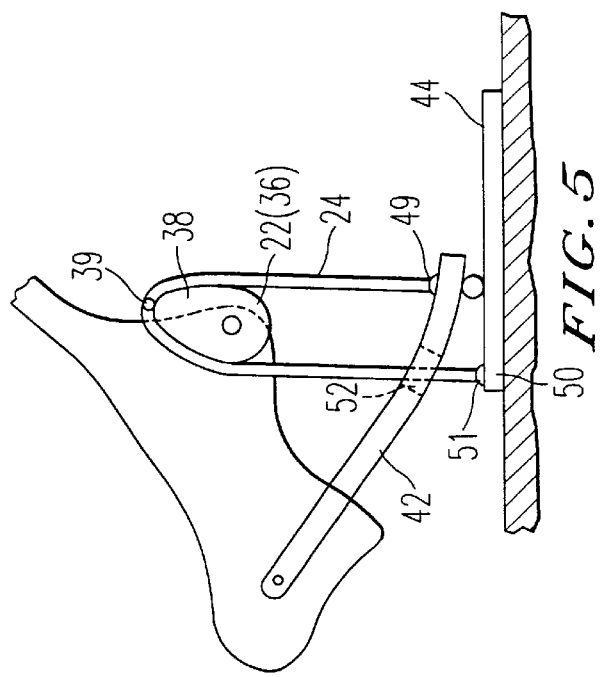
FIG. 5 is a side elevational view of the embodiment shown in FIG. 4 at the beginning of a step.

A prosthetic leg 10 according to the present invention is generally illustrated in FIG. 1. It includes a prosthetic sleeve 12 attached to a base portion 14 and configured to be donned over a stump of an amputee. The base portion 14 provides a connection between the prosthetic sleeve 12 and the moving parts of the prosthetic leg 10. The base portion 14 has an extension 15 through which a shaft 23 extends to secure a rocking member 22 thereto. An energy storing member 16 is secured to a bottom 11 of the base portion 14. A flexible lever member 18 is attached to the energy storing member 16 at hinge 20. The energy storing member 16 may be a leaf spring 26 or any other known energy storage means. The leaf spring 26 may be constructed of any known material appropriate for a spring, such as carbon fiber-reinforced plastic, fiberglass, urethane composites and steel. A line 24 may be made from a strap, cable, cord, rope, or other equivalent element appropriate for transferring energy to and from the leaf spring 26.

Because the lever member 18 is hingedly attached to the leaf spring 26, together they simulate the motion of an ankle. The line 24 has a first end attached to a first point 27 on a front end 28 of the leaf spring 26 while the second end of the line 24 passes through an aperture 25 in the leaf spring 26 and is attached to a second point 29 on a back end 30 of the lever member 18. The line 24 is attached at its midpoint to a tip 39 on the rocking member 22. Note that the distance from the first point 27 to the tip 39 is the same as the distance from the second point 29 to the tip 39. Thus, these two distances are constant and allow the line 24, which is essentially inelastic, to transfer energy back and forth between the lever member 18 and the leaf spring 26. The line 24 is wrapped around the rocking member 22 in a grooved rim such that, as the lever member 18 pivots about hinge 20 in a counterclockwise direction A, the rocking member 22 is also rocked in a counterclockwise direction B, as seen in FIG. 2. Since one end of the line 24 is attached to the front end 28 of the leaf spring 26, the pivoting motion of the lever member 18 is converted into a deflection of the leaf spring 26, thereby storing energy in the leaf spring 26.

As shown in FIG. 2, at the midportion of a step, the lever member 18 is generally straight, i.e. at a relaxed position. As the user moves through a stepping or walking motion, the lever member 18 is flexed and pivoted relative to the leaf spring 26, similar to the pivoting of a foot about an ankle. During midstep, this pivoting motion allows a lower portion 32 of the lever member 18 to remain substantially in contact with the ground 34 while allowing the prosthetic sleeve 12 and the base portion 14 to follow the motion of the stump of a below-the-knee amputee.

When the user completes a stepping or walking motion, as shown in FIG. 3, the energy stored in the leaf spring 26 is returned to the lever member 18. The rocking member 22 may be constructed in the form of either a round wheel or an eccentric body 36, e.g. a cam-shaped wheel with a grooved rim. With the rocking member 22 constructed as the eccentric body 36, it is preferable that the line 24 is fixed at its midpoint to the tip 39 on a lobe 38 of the eccentric body 36. By fixing the line 24 to the tip 39, the eccentric body 36 will be rocked back and forth by the line 24 as the lever member 18 and the leaf spring 26 are flexed and unflexed, respectively.

The amount of force imparted by the lever member 18 to the leaf spring 26 may be modified. For example, it may be preferable to provide more force for a certain user or for users participating in particular activities. Thus, a runner may prefer more force while a walker may prefer less force. Preferably, the line 24 is tensioned between the points 27, 39 and 39, 29 so as to keep the line 24 taut.

Figure 4:
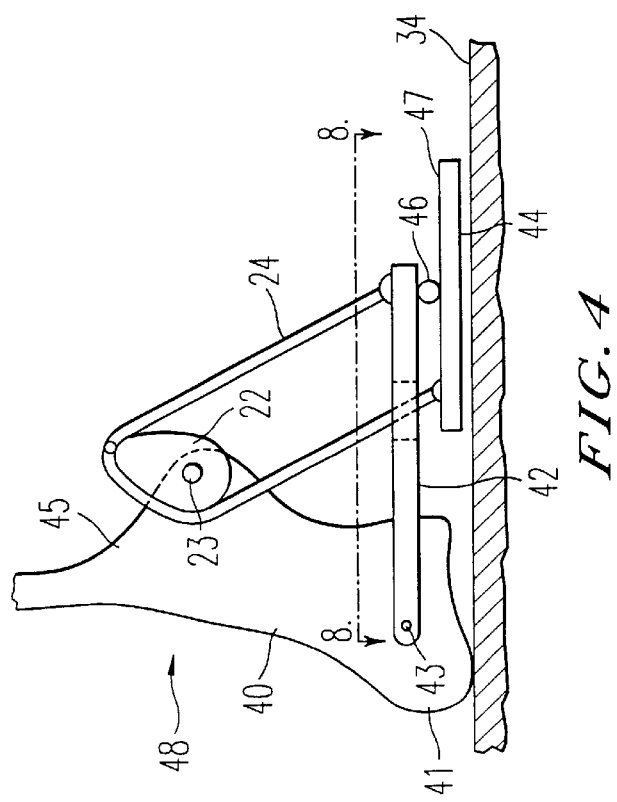
FIG. 4 is a side elevational view of a second embodiment of the present invention in a standing position.

A second embodiment of the present invention is shown in FIGS. 4 through 8. As shown in FIG. 4, a prosthetic foot 48 includes a base portion 40 with a heel 41 and an energy storing member which is a leaf spring 42 secured at its back end by a fastener 43 to the heel 41. The base portion 40 has an extension 45 through which the shaft 23 extends to secure the rocking member 22 thereto. A lever member 44 has a front end which serves as a toe portion 47 of the prosthetic foot 48. The lever member 44 is attached to the leaf spring 42 at a hinge 46. The leaf spring 42 is arranged substantially along a direction extending between the heel 41 and the toe portion 47 of the foot 48. The rocking member 22 and the line 24 have the same construction as in the first embodiment.

Figure 7:
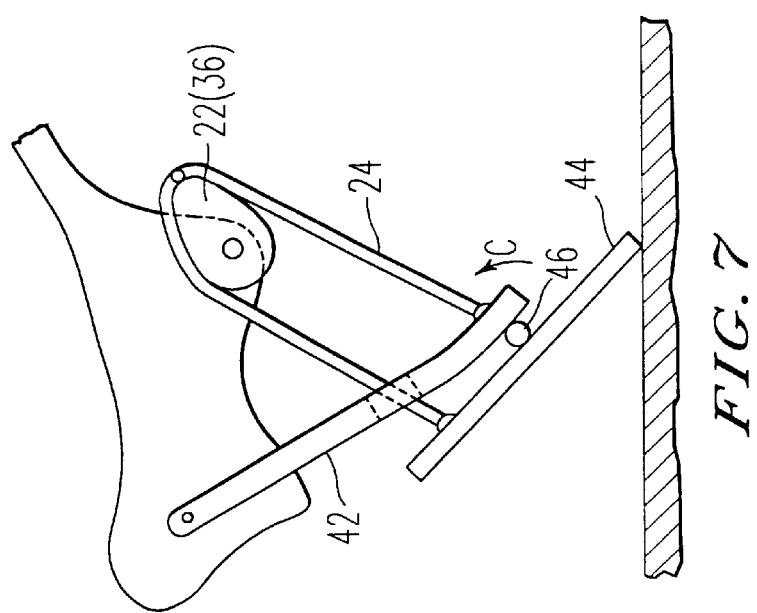
FIG. 7 is a side elevational view of the embodiment shown in FIG. 4 at the completion of a step.
Figure 6:
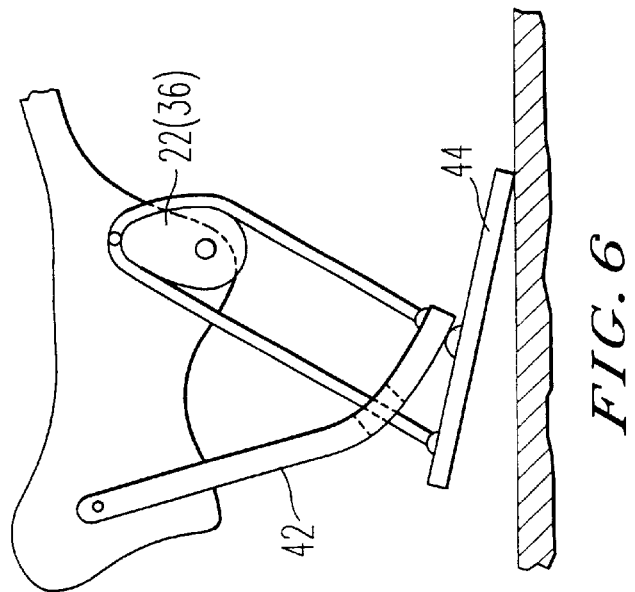
FIG. 6 is a side elevational view of the embodiment shown in FIG. 4 at the midpoint of a step.

In this second embodiment, the foot 48 may be provided with a rubber or plastic cover (not shown) which resembles human skin. The operation of the foot 48, according to this second embodiment, is similar to the leg 10 in the first embodiment. For example, as a user moves through a walking motion, the foot 48 moves from the standing orientation shown in FIG. 4 sequentially to the step orientations shown at the beginning in FIG. 5, at the midpoint in FIG. 6, and then at completion in FIG. 7. As shown in FIG. 5 through 7, and especially in the high stepping position shown in FIG. 7, as the lever member 44 pivots in a counterclockwise direction C around the hinge 46, relative to the leaf spring 42, the pivoting movement of the lever member 44 is converted into a deflection of the leaf spring 42. As a user reaches the end of a walking step, the energy stored in the leaf spring 42 is returned through the line 24 to the lever member 44.

As shown in FIG. 5, a first end of the line 24 extends from a first point 49 on the front end of the leaf spring 42 to the tip 39 of the lobe 38 on the eccentric body 36. The second end of the line extends from a second point 51 on a back end 50 of the lever member 44, through an aperture 52 in the leaf spring 42 to the tip 39 of the lobe 38 on the eccentric body 36.

Figure 8:
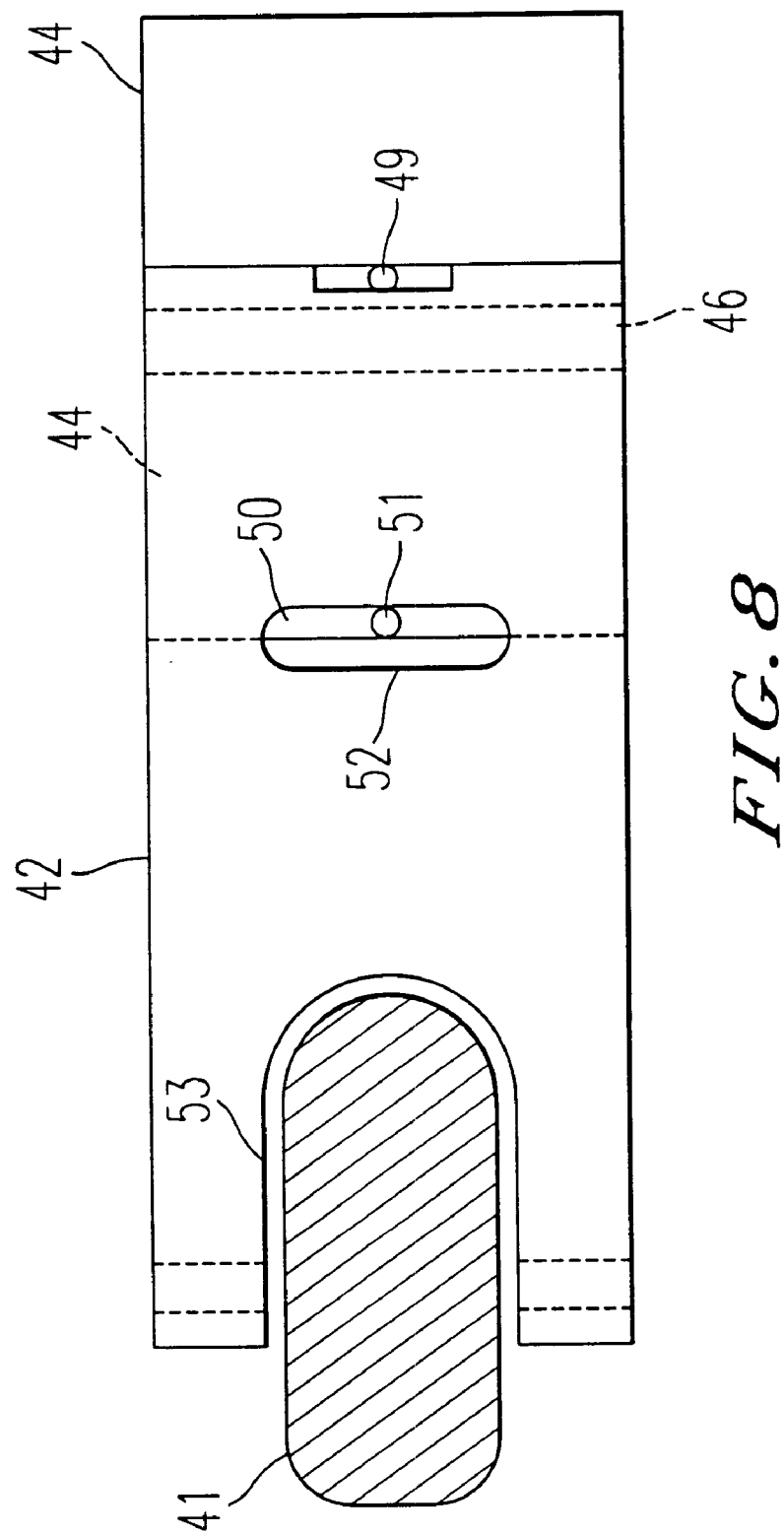
FIG. 8 is a top plan view of the embodiment taken through line 8—8 in FIG. 4.

FIG. 8 shows a top plan view of the leaf spring 42 attached to the lever member 44 by the hinge 46. The leaf spring 42 includes the aperture 52 that is aligned over the second point 51 on the back end 50 of the lever member 44. This arrangement allows the line 24 to pass through the aperture 52 and to be attached to the second point 51. The leaf spring 42 also has a cutout portion 53 for accommodating the heel 41.

Obviously, numerous modifications and variations of the present invention are possible in light of the above teachings. It is therefore to be understood that the invention may be practiced otherwise than as specifically described herein.

What is claimed is:

1. A prosthetic device comprising:
   an energy storing member;
   a lever member flexibly attached to the energy storing member;
   a rocking member; and
   an energy transfer line having a first end attached to the energy storing member and having a second end attached to the lever member, said energy transfer line having a middle portion attached to the rocking member,
   wherein a flexing motion of the lever member is converted into a deflection of the energy storing member and potential energy imparted by the lever member to the energy storing member is stored in the energy storing member, and
   wherein the potential energy stored in the energy storing member is transferred to the lever member via the rocking member.

2. A prosthetic device according to claim 1, wherein the lever member is attached to the energy storing member at a hinge.

3. A prosthetic device according to claim 1, wherein the prosthetic device is a leg and wherein the lever member is positioned for contacting ground.

4. A prosthetic device according to claim 1, wherein the rocking member is a cam-shaped wheel with a grooved rim.

5. A prosthetic device according to claim 1, wherein the middle portion of the energy transfer line is attached to a tip of a lobe on the rocking member.

6. A prosthetic device according to claim 1, further comprising a base portion and a sleeve being attached to the base portion and also being configured to be donned over a stump of an amputee.

7. A prosthetic device according to claim 6, wherein the energy storing member and the rocking member are both attached to the base portion.

8. A prosthetic device according to claim 1, wherein the lever member has a front end and a back end and the energy storing member is a leaf spring having a front end and a back end.

9. A prosthetic device according to claim 8, wherein the lever member is hingedly attached to the front end of the leaf spring.

10. A prosthetic device according to claim 8, wherein the leaf spring has an aperture through which the energy transfer line passes.

11. A prosthetic device according to claim 8, wherein the first end of the energy transfer line is attached to the front end of the energy storing member and the second end of the energy transfer line is attached to the back end of the lever member.

12. A prosthetic device according to claim 8, wherein the prosthetic device is a prosthetic foot and wherein the leaf spring is arranged substantially along a direction extending between a heel portion and a toe portion of the prosthetic foot.

13. A prosthetic device according to claim 12, wherein the back end of the leaf spring is fastened to the heel portion of the prosthetic foot.

14. A prosthetic device comprising an energy storing member, a lever member flexibly attached to the energy storing member, and a rocking member connected between the energy storing member and the lever member,
wherein a flexing motion of the lever member is converted into a deflection of the energy storing member and potential energy imparted by the lever member to the energy storing member is stored in the energy storing member, and
wherein potential energy stored in the energy storing member is transferred to the lever member via the rocking member.

15. A prosthetic device according to claim 14, wherein the rocking member is a cam-shaped wheel.

16. A prosthetic device comprising:
an energy storing member;
a lever member attached to the energy storing member;
a rocking member; and
an energy transfer line having a first end attached to the energy storing member and having a second end attached to the lever member, said energy transfer line having a middle portion attached to the rocking member,
wherein the lever member has a front end and a back end and the energy storing member is a leaf spring having a front end and a back end.

17. A prosthetic device according to claim 16, wherein the lever member is attached to the energy storing member at a hinge.

18. A prosthetic device according to claim 16, wherein the prosthetic device is a leg and wherein the lever member is positioned for contacting ground.

19. A prosthetic device according to claim 16, wherein the rocking member is a cam-shaped wheel with a grooved rim.

20. A prosthetic device according to claim 16, wherein the middle portion of the energy transfer line is attached to a tip of a lobe on the rocking member.

21. A prosthetic device according to claim 16, further comprising a base portion and a sleeve being attached to the base portion and also being configured to be donned over a stump of an amputee.

22. A prosthetic device according to claim 21, wherein the energy storing member and the rocking member are both attached to the base portion.

23. A prosthetic device according to claim 16, wherein the lever member is hingedly attached to the front end of the leaf spring.

24. A prosthetic device according to claim 16, wherein the leaf spring has an aperture through which the energy transfer line passes.

25. A prosthetic device according to claim 16, wherein the first end of the energy transfer line is attached to the front end of the energy storing member and the second end of the energy transfer line is attached to the back end of the lever member.

26. A prosthetic device according to claim 16, wherein the prosthetic device is a prosthetic foot and wherein the leaf spring is arranged substantially along a direction extending between a heel portion and a toe portion of the prosthetic foot.

27. A prosthetic device according to claim 26, wherein the back end of the leaf spring is fastened to the heel portion of the prosthetic foot.

* * * * *